(12) United States Patent
Hwang

(10) Patent No.: US 9,072,707 B2
(45) Date of Patent: Jul. 7, 2015

(54) USE OF C-TERMINAL DOMAIN OF IGFBP-5 COMPRISING HEPARIN-BINDING DOMAIN AS AN ANGIOGENESIS INHIBITOR

(71) Applicant: RESEARCH & BUSINESS FOUNDATION SUNGKYUNKWAN UNIVERSITY, Suwon-si (KR)

(72) Inventor: Jae Ryoung Hwang, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/049,621

(22) Filed: Oct. 9, 2013

(65) Prior Publication Data

US 2014/0100160 A1   Apr. 10, 2014

(30) Foreign Application Priority Data

Oct. 9, 2012 (KR) .......................... 10-2012-0112111

(51) Int. Cl.
*A61K 38/10* (2006.01)
*A61K 38/18* (2006.01)

(52) U.S. Cl.
CPC .................. *A61K 38/18* (2013.01); *A61K 38/10* (2013.01)

(58) Field of Classification Search
CPC ............................... A61K 38/10; A61K 38/18
See application file for complete search history.

(56) References Cited

U.S. PATENT DOCUMENTS

| 5,712,381 | A  | * | 1/1998  | Lin et al. ..................... 536/23.5 |
| 8,552,148 | B2 | * | 10/2013 | Lee et al. ..................... 530/324 |
| 2002/0142963 | A1 | * | 10/2002 | Andress ......................... 514/12 |
| 2009/0048158 | A1 | * | 2/2009  | Moreno et al. ................. 514/12 |

FOREIGN PATENT DOCUMENTS

| KR | 10-1992-7001422 A | 8/1992 |
| KR | 10-2011-0044992 A | 5/2011 |
| WO | WO 99/32620 | * 7/1999 |

OTHER PUBLICATIONS

Kim et al., Bull. Korean Chem. Soc. 2010, vol. 31, No. 7 2019-2024; DOI 10.5012/bkcs.2010.31.7.2019.*
Bramani et al., Journal of Molecular Endocrinology, 23, 117-123, 1999.*
Allan et al., Endocrinology 147: 338-349, 2006.*
Akkiprik et al., Breast Cancer Research 2008, 10:212 (doi:10.1186/bcr2116).*
Abrass et al., Am. J. Physiol. 273 (Renal Physiol. 42): F899-F906, 1997.*
Rho, Seung Bae, et al. "Insulin-like growth factor-binding protein-5 (IGFBP-5) acts as a tumor suppressor by inhibiting angiogenesis." *Carcinogenesis* vol. 29.No. 11 (Sep. 4, 2008) pp. 2106-2111.
Twigg, Stephen M., et al. "Insulin-like Growth Factor-binding Protein 5 Complxes with the Acid-labile Subunit." *Journal of Biological Chemistry* vol. 273.No. 44 (Oct. 30, 1998) pp. 28791-28798.
Korean Notice of Allowance issued on Jan. 2, 2015 in counterpart Korean Application No. 10-2013-0120155 (2 pages, in Korean).

* cited by examiner

*Primary Examiner* — Marianne P Allen
(74) *Attorney, Agent, or Firm* — NSIP Law

(57) ABSTRACT

The present invention relates to a pharmaceutical composition for inhibiting angiogenesis comprising an isolated peptide comprising the heparin-binding domain of insulin-like growth factor-binding protein-5 (IGFBP-5), a method for inhibiting angiogenesis using the peptide, a pharmaceutical composition for the prevention or treatment of cancer comprising the peptide, a method for treating cancer using the peptide, a novel angiogenesis-inhibiting peptide derived from heparin-binding domain of IGFBP-5, a polynucleotide encoding the peptide, an expression vector comprising the polynucleotide and a transformant comprising the vector.

6 Claims, 10 Drawing Sheets

FIG. 3
A.
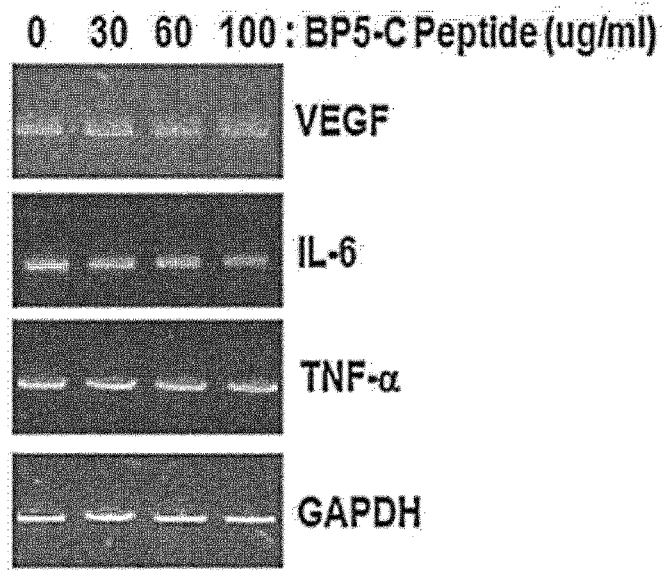
B.
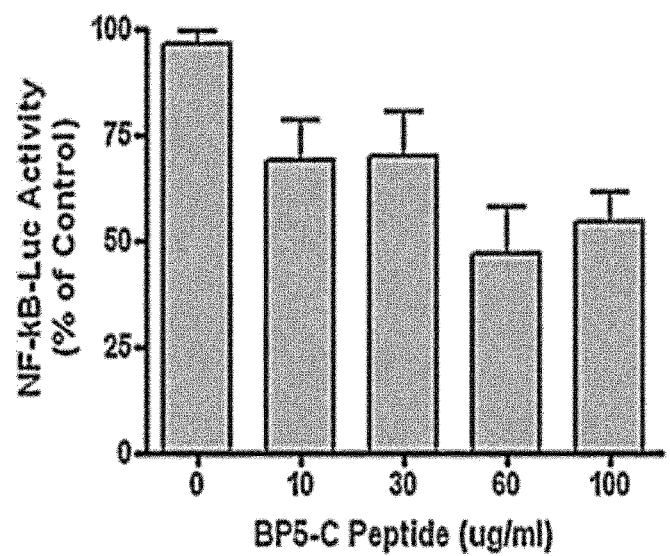

FIG.4

```
1    MLPRVGCPALPLPPPPLLPLLPLLLLLLGASGGGGGARAEVLFRCPPCTPERLAACGPPP    60   BP2
1    ------------------MVLLTAVLLLLAAYAG-PAQSLGSFVHCEPCDEKALSHCPPSP   42   BP5
                       : **. :****.* .*  .     :.:* **  : *: * *.*

61   VAPPAAVAAVAGGARMPCAELVREPGCGCCSVCARLEGEACGVYTPRCGQGLRCYPHPGS   120  BP2
43   LG-----------------CELVKEPGCGCCHTCALAEGQSCGVYTERCAQGLRCLPRDE   86   BP5
     :.                 .***:******* .**  **:;***** **.***** *:  ..

121  ELPLQALVHGEGTCEKRRDAEYGASPEQVADNGDDHSEGGLVENHVDSTHNHLGGGGSAG  180  BP2
87   EKPLHALLHGRGVCLNEKSYREQVKIERDSREHEEPTTSEHAEETYSPKIFRP----KHT  142  BP5
     * **:**: *.*.* :.:. .  .. *: :  : :: : . :.*: .. ..:  .
```

Heparin-binding domain in BP2

```
181  RKPLKSGHKELAVFREKVTEQHRQHGKGQ KHHLGLEEPKKLR PPPAR TPCQQELDQVLER  240  BP2
143  RISELKAEAVKKDRRKKLTQSKFVGGAEN TAHPRTISAPEHRQESEQ GPCRRHHEASLQE  202  BP5
     *  .  ..    *:*:*:..:    *   .. *  : .. ::*  . : **:::.:: *:.

241  ISTHRLPDERGPLEHLYSLHIPNCD KH GL YNLH QC KHSLNGQR GECWCVNPNTGKLIQGA  300  BP2
203  LKAS-------PRHVPRAVYLPNCD RH GF YKRH QC KPSRGRKF GICWCVD-KYGHKLPGH  254  BP5
     :.*        ::::: * .::**  ::  . :  ::  *   ..: *:*** . : :..

301  PTIRGDPECHLFYNEQQEARGVHTQRHQ   328  BP2        C-domain
255  EYVDGDFQCHTFDSSNVE----------   272  BP5
```

FIG. 5
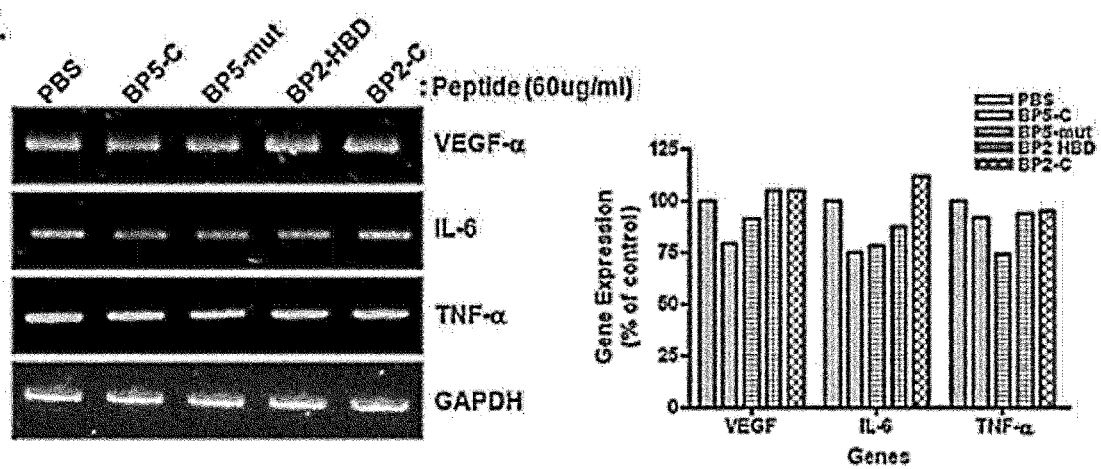
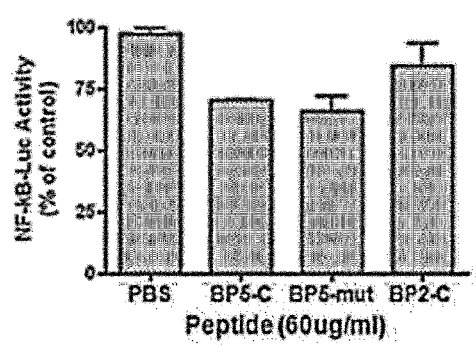

US 9,072,707 B2

USE OF C-TERMINAL DOMAIN OF IGFBP-5 COMPRISING HEPARIN-BINDING DOMAIN AS AN ANGIOGENESIS INHIBITOR

CROSS-REFERENCE TO RELATED APPLICATIONS

This application claims the benefit under 35 USC 119(a) of Korean Patent Application No. 10-2012-0112111 filed on Oct. 9, 2013, in the Korean Intellectual Property Office, the entire disclosure of which is incorporated herein by reference for all purposes.

SEQUENCE LISTING

The instant application contains a Sequence Listing which has been submitted electronically in ASCII format and is hereby incorporated by reference in its entirety. Said ASCII copy, created on Nov. 8, 2013, is named 042092.0013_SL.txt and is 11,956 bytes in size.

BACKGROUND OF THE INVENTION

1. Field of the Invention

The present invention relates to a pharmaceutical composition for inhibiting angiogenesis comprising an isolated peptide comprising the heparin-binding domain of insulin-like growth factor-binding protein-5 (IGFBP-5), a method for inhibiting angiogenesis using the peptide, a pharmaceutical composition for the prevention or treatment of cancer comprising the peptide, a method for treating cancer using the peptide, a novel angiogenesis-inhibiting peptide derived from heparin-binding domain of IGFBP-5, a polynucleotide encoding the peptide, an expression vector comprising the polynucleotide and a transformant comprising the vector.

2. Description of the Prior Art

Insulin-like growth factor-binding protein-5 (IGFBP-5), a member of the IGF (insulin-like growth factor) binding protein family, is known to play an important role in various cellular functions, including cell proliferation. IGFBP-5 is localized to the nucleus due to its NLS (nuclear localization signal) and is also secreted extracellularly. However, studies on the functions of IGFBP-5 in the nucleus and the functions of extracellularly secreted IGFBP-5 have not yet been sufficient. It was recently reported that IGFBP-5 functions as a transactivator in the nucleus.

Specifically, IGFBP-5 consists largely of three domains: N-terminal domain, L-domain, and C-terminal domain. An IGF-binding site is located in the N-terminal domain, and an NLS is located in the C-terminal domain. In addition, a heparin-binding site is located in both the L-domain and the C-terminal domain. The glycosylation and phosphorylation of IGFBP-5 are known to inhibit the heparin binding of IGFBP-5, but the exact biological significance of the glycosylation and phosphorylation has not yet been established.

As is known in the art, IGFBP-5 modulates the functions of IGF-I and IGF-II by inhibiting the binding of IGF-I or IGF-II to their receptors, but IGF-independent functions of IGFBP-5 were also reported. In addition, in the results of studies performed using IGFBP-5 transgenic mice and knockout mice, IGFBP-5 transgenic mice showed high neonatal mortality, growth inhibition and delayed muscle development. Further, IGFBP-5 transgenic female mice showed sterility and premature cell death in the mammary glands. In addition, IGFBP-5 knockout mice demonstrated delayed mammary gland involution. Such results suggest that IGFBP-5 can induce apoptosis.

Angiogenesis is the process by which new blood vessels are formed from existing blood vessels and an elaborate network is formed by way of a variety of complex mechanisms. Typical known examples include a mechanism by which an angiogenic factor acts on the receptor of vascular endothelial cells to induce the proliferation of vascular endothelial cells, a mechanism that is involved in the migration of vascular endothelial cells by secretion of matrix metalloproteinase, a mechanism that is involved in the adhesion of vascular endothelial cells, and the like. Angiogenesis is essential for normal development, that is, fetal development, reproductive cycles, growth, and wound healing, and is also involved in the progression of diseases such as cancer and diabetic retinopathy.

For the treatment of angiogenesis-related diseases such as cancer, studies on the inhibition of angiogenesis have been actively conducted. Particularly, there have been studies on methods of administering antagonists in order to inhibit the activities of VEGF (vascular endothelial growth factor) and bFGF (basic fibroblast growth factor) known to be potent angiogenesis inducers in angiogenic processes, and methods of controlling the expression of integrin in vascular endothelial cells in order to inhibit the metastasis of cancer cells. In particular, VEGF is the most potent angiogenesis inducer that shows various biological activities by binding to its two receptors (VEGFR1 and VEGFR2) present on the surface of endothelial cells and plays a pivotal role in both vasculogenesis and angiogenesis. Thus, studies on drugs that inhibit angiogenesis by reducing the expression and signaling of VEGF have been actively conducted.

DISCLOSURE

Technical Problem

Accordingly, the present inventors have made extensive efforts to find peptides capable of effectively inhibiting angiogenesis by reducing the expression and signaling of VEGF, and as a result, have found that the C-terminal domain of IGFBP-5, particularly a heparin-binding domain located in the C-terminal domain, has an effect capable of effectively inhibiting angiogenesis, and thus a peptide comprising the heparin-binding domain can be used for the treatment of patients with diseases such as cancer in need of the inhibition of angiogenesis. Further, the present inventor has developed a novel peptide from the heparin-binding domain of IGFBP-5, and confirmed the angiogenesis-inhibiting activity thereof, thereby completing the present invention.

Technical Solution

It is an object of the present invention to provide a pharmaceutical composition for inhibiting angiogenesis, comprising an isolated peptide comprising the heparin-binding domain of insulin-like growth factor-binding protein-5 (IGFBP-5) as an active ingredient.

Another object of the present invention is to provide a method of inhibiting angiogenesis using the peptide.

Still another object of the present invention is to provide a pharmaceutical composition for preventing or treating cancer, comprising the peptide as an active ingredient.

Still another object of the present invention is to provide a method of treating cancer using the peptide.

Yet another object of the present invention is to provide a novel angiogenesis-inhibiting peptide derived from the heparin-binding domain of IGFBP5, a polynucleotide encoding the peptide, an expression vector comprising the polynucleotide, and a transformant comprising said expression vector.

BEST MODE

In one aspect, the present invention provides a pharmaceutical composition for inhibiting angiogenesis, comprising an isolated peptide comprising the heparin-binding domain of insulin-like growth factor-binding protein-5 (IGFBP-5) as an active ingredient.

As used herein, the term "IGFBP-5" refers to a protein belonging to the IGFBP family and known to play an important role in various cellular functions, including cell proliferation. IGFBP-5 consists of an N-terminal domain, an L domain and a C-terminal domain, which can perform different functions. As used herein, "N-terminal domain" means a domain consisting of amino acids 1-80 (numbered from the first amino acid following the signal peptide consisting of 20 amino acids from the N-terminus) of the amino acid sequence of IGFBP-5, "L-domain" means a domain consisting of amino acids 81-168 of the amino acid sequence, and "C-terminal domain" means a domain consisting of amino acids 169-252 of the amino acid sequence, but the scope of the present invention is not limited thereto. The amino acid sequences of the C-terminal domain, the L-domain and the N-terminal domain are set forth in SEQ ID NOS: 1 to 3, respectively. Information on the IGFBP-5 protein can be obtained from public databases such as NCBI GenBank. For example, the IGFBP-5 protein may be a protein deposited under accession No. NP_000590, but is not limited thereto. The present inventors have found that the C-terminal domain among the above three domains has a remarkable effect of inhibiting cancer growth by specifically inhibiting angiogenesis, unlike other domains, and particularly, a heparin-binding domain located in the C-terminal domain shows this effect. This effect of the C-terminal domain has not yet been known and was first found by the present inventors.

As used herein, the phrase "heparin-binding domain of IGFBP-5" means a heparin-binding domain located in the C-terminal domain of the IGFBP-5 protein. For the purpose of the present invention, "heparin-binding domain" means an IGFBP-5-derived domain" capable of inhibiting angiogenesis and cancer growth. The heparin-binding domain derived from IGFBP-5 can exhibit a specific effect of inhibiting angiogenesis and cancer growth, unlike the heparin-binding domains of other proteins. In an example of the present invention, it was shown that a heparin-binding domain derived from IGFBP-2 did not exhibit an angiogenesis inhibitory effect, whereas the heparin-binding domain of IGFBP5 of the present invention could exhibit an angiogenesis inhibitory effect (FIGS. 4 to 6).

Specifically, the heparin-binding domain is located in the 201-218 amino acid domain of the amino acid sequence of IGFBP-5 (SEQ ID NO: 4). In the 201-218 amino acid domain, an IGF-1-binding domain comprising the amino acid glycine at position 203 and the amino acid glutamine at position 209 is also located, but the heparin-binding domain can exhibit the effect of inhibiting angiogenesis and cancer growth, even though the kinds of amino acids at positions 203 and 209 are alanine (A). Thus, the angiogenesis inhibiting effect of the 201-218 amino acid domain is attributable to the heparin-binding domain. In addition, the scope of the heparin-binding domain of IGFBP-5 according to the present invention comprises, in addition to, the amino acid sequence of SEQ ID NO: 4, any biological sequence that has a sequence identity of at least 70%, preferably at least 80%, more preferably at least 90%, even more preferably at least 95%, still even more preferably at least 98%, and more preferably at least 99%, with the amino acid sequence of SEQ ID NO: 4, and can substantially inhibit angiogenesis or cancer growth. Thus, peptide variants having a deletion, modification, substitution or addition of some amino acids of the amino acid sequence of SEQ ID NO: 4 also fall within the scope of the present invention, as long as they have the sequence identity as described above and have the activity of substantially inhibiting angiogenesis or cancer growth. Examples of the peptide variants include, but are not limited to, an amino acid sequence set forth in SEQ ID NO: 5.

Preferably, the heparin-binding domain according to the present invention may comprise an amino acid sequence represented by the following formula 1:

[N-terminus—R K X1 F Y K R K X2 C K P S R G R K R—C-terminus] (SEQ ID NO: 16)    Formula 1 wherein X1 and X2 are any amino acids.

Amino acids mentioned herein are abbreviated according to the nomenclature rules of IUPAC-IUB as follows:

| Alanine | A; | Arginine | R; |
| Asparagine | N; | Aspartic acid | D; |
| Cysteine | C; | Glutamic acid | E; |
| Glutamine | Q; | Glycine | G; |
| Histidine | H; | Isoleucine | I; |
| Leucine | L; | Lysine | K; |
| Methionine | M; | Phenylalanine | F; |
| Proline | P; | Serine | S; |
| Threonine | T; | Tryptophan | W; |
| Tyrosine | Y; | Valine | V. |

Because the heparin-binding domain of the present invention results in the inhibition of angiogenesis and cancer regardless of IGF-I binding, the kinds of amino acids X1 and X2 in formula 1 that are involved in IGF-I binding are not specifically limited. However, preferably, X1 may be glycine or alanine, and X2 may be glutamine or alanine. In an example of the present invention, it was shown that a BP5-C peptide, which is a representative heparin-binding domain and in which X1 in formula 1 is glycine and X2 is glutamine, and a BP5-mut peptide in which X1 and X2 in formula 1 are alanine, inhibited the expression of VEGF, IL-6 and TNF-alpha, which are major regulators of angiogenesis, regardless of IGF-I binding (FIGS. 4 and 5). In addition, these peptides inhibited angiogenesis (FIGS. 6 and 8).

As used herein, the phrase "peptide comprising the heparin-binding domain of IGFBP-5" means a peptide that essentially comprises the heparin-binding domain of IGFBP-5 and has 18-84 amino acids, preferably 18-59 amino acids, and more preferably 18-32 amino acids. The peptide is a peptide comprising the sequence of formula 1, and more preferably a peptide having an amino acid sequence set forth in SEQ ID NO: 1, 4 or 5, but is not limited thereto. In an example of the present invention, it was shown that a peptide (SEQ ID NO: 4 or 5) comprising a heparin-binding domain consisting of 18 amino acids, and a peptide (C-terminal domain; SEQ ID NO: 1) comprising a heparin-binding domain consisting of 84 amino acids, could significantly inhibit the expression of VEGF, IL-6 and TNF-alpha, inhibit NF-kB activity, and also effectively inhibit angiogenesis and cancer growth.

The inventive peptide comprising the heparin-binding domain of IGFBP-5 may be a peptide amidated at the C-terminus.

In order to protect a peptide from proteases in vivo and increase the stability thereof, the amino and carboxyl termini of the peptide may be modified or protected with various organic groups. Thus, the C-terminus of the inventive peptide may be modified, and the modification is not specifically limited, but may be, for example, amidation.

The peptide of the present invention may be prepared according to a method well known in the art. For example, it may be synthesized using an automated peptide synthesizer or it may be produced by a genetic engineering technique. For instance, after producing a fusion gene encoding a fusion protein comprising a fusion partner and the peptide of the present invention through genetic manipulation, transforming a host cell with the fusion gene, and expressing the fusion protein in the host cell, the peptide of the present invention may be cleaved and isolated from the fusion protein using an adequate protease or compound, thereby producing a desired peptide. For this end, a DNA sequence coding for an amino acid residue that can be cleaved by a protease such as factor Xa or enterokinase or a compound such as CNBr or hydroxylamine may be inserted between the fusion partner and a polynucleotide encoding the peptide of the present invention.

Because the peptide of the present invention effectively inhibits angiogenesis, a composition comprising the peptide as an active ingredient can be effectively used for the inhibition of angiogenesis and the prevention or treatment of angiogenesis-related diseases.

As used herein, the term "inhibiting angiogenesis" means inhibiting the process in which new blood vessels are formed from the existing blood vessels. For the purpose, the term means inhibiting angiogenesis by reducing the expression and activity of major factors, such as VEGF, IL-6 or TNF-alpha, which are involved in angiogenesis.

As used herein, the term "angiogenesis-related diseases" refers to diseases that develop or progress as angiogenesis increases. For the purpose of the present invention, the term includes any diseases that are treated by the peptide of the present invention. Examples of the angiogenesis-related diseases include, but are not limited to, diabetic retinopathy, retinopathy of prematurity, corneal transplant rejection, neovascular glaucoma, erythrosis, proliferative retinopathy, psoriasis, hemophilic arthropathy, capillary proliferation in atherosclerotic plaques, keloid, wound granulation, vascular adhesions, rheumatoid arthritis, osteoarthritis, autoimmune diseases, Crohn's disease, restenosis, atherosclerosis, intestinal adhesions, cat scratch disease, ulcer, cirrhosis, glomerulonephritis, diabetic nephropathy, malignant nephrosclerosis, thrombotic microangiopathy, organ-transplant rejection, glomerulopathy, diabetes, inflammatory diseases or neurodegenerative diseases.

As used herein, the term "prevention" refers to all actions that inhibit or delay the development of angiogenesis-related disease by administering the composition, and the term "treatment" refers to all actions that restore or beneficially change the symptoms of angiogeness-related by administering the composition.

The pharmaceutical composition comprising the peptide of the present invention may further comprise a pharmaceutically acceptable carrier, excipient or diluent that is generally used in the preparation of pharmaceutical compositions.

The pharmaceutical composition may have any one formulation selected from the group consisting of a tablet, a pill, powder, granules, a capsule, a suspension, a solution, an emulsion, a syrup, a sterilized aqueous solution, a non-aqueous solution, a suspension, an emulsion, a lyophilized formulation, and a suppository. In addition, the pharmaceutical composition may be in the form of various oral or parenteral formulations. The pharmaceutical composition is formulated using conventional diluents or excipients, including fillers, extenders, binders, wetting agents, disintegrants, and surfactants. Solid formulations for oral administration include tablets, pills, powders, granules, capsules, etc. These solid formulations may be prepared by mixing at least one compound with one or more excipients, for example, starch, calcium carbonate, sucrose, lactose, gelatin, etc. In addition to simple excipients, lubricants such as magnesium stearate or to may also be used. In addition, liquid formulations for oral administration include a suspension, a solution, an emulsion and a syrup, etc. In addition to water commonly used as a simple diluent and liquid paraffin, various excipients, for example, wetting agents, sweetening agents, flavors, preservatives, etc. may be included. Formulations for parenteral administration include sterilized aqueous solutions, non-aqueous solvents, suspending agents, emulsions, freeze-drying agents, suppositories, etc. Propylene glycol, polyethylene glycol, vegetable oils such as olive oil, injectable esters such as ethyl oleate, etc. may be used as non-aqueous solvents and suspending agents. Bases for suppositories may include witepsol, macrogol, tween 61, cacao butter, laurin butter, glycerinated gelatin, etc.

The pharmaceutical composition of the present invention may be administered in a pharmaceutically effective amount.

As used herein, the term "pharmaceutically effective amount" refers to an amount sufficient to treat diseases, at a reasonable benefit/risk ratio applicable to any medical treatment. The effective dosage level of the composition may be determined depending on the subject's type, the disease severity, the subject's age and sex, the activity of the drug, sensitivity to the drug, the time of administration, the route of administration, excretion rate, the duration of treatment, drugs used in combination with the composition, and other factors known in the medical field. The pharmaceutical composition of the present invention may be administered alone or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this minimum amount can be easily determined by those skilled in the art. The preferred dose of the composition of the present invention can vary depending on the patient's condition and weight, the severity of the disease, the form of the drug, and the route and period of administration. The composition may be administered once or several times a day. The composition may be administered to various mammals, including rats, humans, domestic animals and the like, by various routes. The composition may be administered by any conventional method known in the art. For example, the composition may be administered orally, intrarectally or by intravenous, intramuscular, subcutaneous, intrauterine, intrathecal or endovascular injection.

In an example of the present invention, it was shown that, unlike the L-domain and the N-terminal domain, the C-terminal domain of IGFBP-5 effectively inhibited the expression of VEGF, IL-6 and TNF-alpha, which are involved primarily in angiogenesis and cancer growth, and it effectively inhibited the activity of NF-kB that is a major signaling factor in cancer (FIG. 1). Further, the C-terminal domain of IGFBP-5 exhibited remarkable anticancer effects compared to a control group, the L-domain and the N-terminal domain (FIG. 2). In addition, the present inventors found that, of the C-terminal domain, the 201-218 amino acid domain (BP5-C peptide) showing angiogenesis inhibitory and cancer inhibitory effects plays an important role (FIG. 3). In addition, the present inventors compared the effect of the heparin-binding domain of IGFBP-5 with those of an IGFBP-2-derived heparin binding domain (BP2-HBD) and an IGF-I binding domain (BP2-C) in order to examine whether the effect of the heparin-binding domain of IGFBP-5 is specific. As a result, it was shown that BP2-HBD and BP2-C had no effect on the expression of VEGF, IL-6 and TNF-alpha, the inhibition of NF-kB activity and the inhibition of angiogenesis, whereas the inventive peptide comprising the heparin-binding domain of IGFBP-5 effectively inhibited the expression of the above genes, NF-kB activity and angiogenesis (FIGS. 4 to 6). In addition, a BP5-mut peptide obtained by mutating the IGF-I binding site of the 201-218 amino acid domain also showed the effects of inhibiting the expression of genes such as VEGF and inhibiting angiogenesis, suggesting that the heparin-binding domain in the 201-218 amino acid domain is a specific site capable of exhibiting the above-described effects (FIGS. 5 and 6). Further, it was shown that the BP5-C peptide representative of the inventive peptides comprising the heparin-binding domain exhibited a remarkable anticancer effect, indicating that the peptide of the present invention can be effectively used for the prevention or treatment of cancer (FIG. 7). In addition, the influence of the inventive peptide on blood vessel sprouting was examined using a rat aortic ring, and as a result, it was shown that the inventive peptide effectively inhibited blood vessel sprouting, unlike a comparative group.

In still another aspect, the present invention provides a method of inhibiting angiogenesis using the above peptide.

Herein, the peptide and the inhibition of angiogenesis are as described above.

Specifically, the treatment method of the present invention comprises administering a therapeutically effective amount of the pharmaceutical composition to a subject in need of the inhibition of angiogenesis. Examples of the subject include, but are not limited to, mammals, including dogs, cattle, horses, rabbits, mice, rats, chickens or humans. The pharmaceutical composition may be administered parenterally, subcutaneously, intraperitoneally, intrapulmonarily or intranasally. For topical treatment, the pharmaceutical composition may be administered by suitable methods, including intralesional injection. The preferred dose of the pharmaceutical composition of the present invention varies depending on the subject's condition and weight, the severity of the disease, the form of the drug, and the route and period of administration and can be suitably selected by those skilled in the art.

In still another aspect, the present invention provides a pharmaceutical composition for preventing or treating cancer, comprising the heparin-binding domain of IGFBP-5 as an active ingredient.

Herein, IGFBP-5, the heparin-binding domain of IGFBP-5, peptide, preventing and treating are as described above.

As used herein, the term "cancer" refers to any kind of cancer that can be treated by the peptide of the present invention. Examples of cancer that can be treated by inhibiting angiogenesis using the peptide of the present invention include, but are not limited to, esophageal cancer, stomach cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, brain cancer, thyroid cancer, leukemia, Hodgkin's disease, lymphoma, multiple myeloma, or blood cancer.

In an example of the present invention, it was shown that the inventive peptide comprising the heparin-binding domain of IGFBP-5 could inhibit cancer by inhibiting angiogenesis, suggesting that the inventive peptide can be effectively used for the prevention or treatment of cancer (FIGS. 1 to 7).

In another aspect, the present invention provides a method of treating cancer using the above peptide.

Herein, the peptide and cancer are as described above.

Specifically, the treatment method of the present invention comprises administering a therapeutically effective amount of the pharmaceutical composition to a subject suspected of having cancer. Examples of the subject include, but are not limited to, mammals, including dogs, cattle, horses, rabbits, mice, rats, chickens or humans. The pharmaceutical composition may be administered parenterally, subcutaneously, intraperitoneally, intrapulmonarily or intranasally. For topical treatment, the pharmaceutical composition may be administered by suitable methods, including intralesional injection. The preferred dose of the pharmaceutical composition of the present invention varies depending on the subject's condition and weight, the severity of the disease, the form of the drug, and the route and period of administration and can be suitably selected by those skilled in the art.

In another aspect, the present invention provides a novel angiogenesis-inhibiting peptide derived from the heparin-binding domain of IGFBP-5.

The heparin-binding domain of IGFBP-5 and angiogenesis are as described above.

In the present invention, when both $203^{th}$ and $209^{th}$ amino acid residues of the heparin-binding domain of IGFBP-5 ($201^{th}$ to $218^{th}$ amino acid residues of IGFBP-5, SEQ ID NO: 4) have been substituted to alanine (A), the resulting mutated peptide (SEQ ID NO: 5) exhibit angiogenesis-inhibiting activity.

Therefore, in the present invention provides an isolated peptide having activity of inhibiting angiogenesis consisting of an amino acid sequence of SEQ ID NO: 5.

In another aspect, the present invention provides composition comprising the above peptide.

The peptide is as described above, and the composition may be a pharmaceutical composition.

When the composition is a form of pharmaceutical composition, it can be a pharmaceutical composition for inhibiting angiogenesis, preventing or treating angiogenesis-related disease, or preventing or treating cancer, but not limited thereto.

In another aspect, the present invention provides a polynucleotide encoding said peptide, an expression vector comprising said polynucleotide, and a transformant including the expression vector.

Herein, the peptide is as described above.

An expression vector comprising a polynucleotide encoding the inventive peptide comprising the heparin-binding domain of IGFBP-5 is not specifically limited, but may be a vector capable of replicating and/or expressing the polynucleotide in eukaryotic or prokaryotic cells, including mammalian cells (e.g., human, monkey, rabbit, rat, hamster or mouse cells), plant cells, yeast cells, insect cells and bacterial cells (e.g., *E. coli*). Preferably, it may be a vector, which comprises at least one selective marker and is operably linked to a suitable promoter so that the polynucleotide can be expressed in a host cell. For example, the vector may comprise the polynucleotide introduced into a phage, plasmid, cosmid, mini-chromosome, virus or retrovirus vector.

Cells into which the expression vector of the present invention is to be introduced to form transformants include bacterial cells such as *E. coli, Streptomyces* and *Salmonella typhimurium*; yeast cells; fungal cells such as *Pichia pastoris*; insect cells such as *Drosophila* or *Spodoptera* Sf9 cells; animal cells such as Chinese hamster ovary (CHO) cells, SP2/0

(mouse myeloma), human lymphoblastoid, COS, NSO (mouse myeloma), 293T, Bowes melanoma cells, HT-1080, BHK (baby hamster kidney cells), HEK (human embryonic kidney cells), PERC.6 (human retinal cells), and the like; and plant cells.

As used herein, the term "introduction" refers to the delivery of the vector comprising the polynucleotide encoding the inventive peptide into a host cell. This introduction may be performed by various methods known in the art, including calcium phosphate-DNA coprecipitation, DEAE-dextran-mediated transfection, polybrene-mediated transfection, electroporation, microinjection, liposome-mediated transfection, liposome fusion, lipofection and protoplast fusion. Also, term "transfection" means delivering a desired material into a cell by means of infection using viral particles. In addition, the vector may be introduced into a host cell by gene bombardment. In the present invention, the term "introduction" may be used interchangeably with transfection.

The Effect of the Present Invention

The peptide of the present invention shows excellent angiogenesis-inhibiting activity and anti-cancer effects. In addition, because of low molecular weight, it has the advantage of infiltration into blood vessels and tissues, thereby being useful in treating diseases such as cancer or several ophthalmologic diseases.

BRIEF DESCRIPTION OF THE DRAWINGS

FIG. 1A shows the results obtained by constructing a 2774 ovarian cancer cell line that stably expresses each of the domains of IGFBP-5, and then examining the expression of the domains in the cell line in WCL (whole cell lysate) and CM (conditioned media); FIG. 1B shows the results of RT-PCR analysis for the expression of VEGF and cytokine in a 2774 cell line that stably expresses a truncation mutant of IGFBP-5; and FIG. 1C shows the results obtained by transfecting each BP5/2774 cell line with an NF-kB-RE-Luc reporter plasmid and a *Renilla* luciferase-expressing plasmid, and then examining NF-kB activity in the cell line.

FIG. 2a is a photograph showing the results obtained by injecting nude mice subcutaneously with a 2774 cell line that stably expresses each of the domains of IGFBP-5, and then measuring the tumor volume of the mice.

FIG. 3 shows the inhibitory effect of a peptide derived from the C-terminal domain of IGFBP-5 against the expression of VEGF and cytokines. FIG. 3A shows the results obtained by treating the 2774 ovarian cell line with a peptide (BP5-C) derived from the C-terminal domain of IGFBP-5 at concentrations of 30, 60 and 100 µg/ml, and then analyzing the expression of VEGF and cytokines in the cells by RT-PCR, and FIG. 3B is a bar graph diagram showing the results obtained by treating the 2774 cell line with various concentrations of the BP5-C peptide, and then measuring NF-kB activity in the cell line by an NF-kB-RE-Luc assay. In FIG. 3, '0' indicates treatment with PBS in place of the peptide, and NF-kB activity is expressed as a percentage relative to 100% for treatment with PBS.

FIG. 4 shows the results of sequence alignment of IGFBP-2 (SEQ ID NO: 17) and IGFBP-5 (SEQ ID NO: 18).

FIG. 5 shows the inhibitory effect of the heparin-binding domain of IGFBP-5 against the expression of VEGF and cytokines. Specifically, the left panel of FIG. 5A shows the results obtained by treating the 2774 cell line with 60 µg/ml of each of a peptide (BP5-C) derived from the C-terminal domain of IGFBP-5, a peptide (BP5-mut) obtained by mutating the IGF-1-binding domain, a peptide (BP2-HBD) for the heparin-binding domain of IGFBP-2, and a peptide (BP2-C) for the C-terminal domain of IGFBP-2, isolating RNA from the cell line, and analyzing the influence of each of the peptides on the expression of VEGF and cytokines by RT-PCR, and the right panel of FIG. 5A is a bar graph diagram showing the results obtained by scanning bands resulting from RT-PCR, and then expressing the percentages of the bands relative to 100% for PBS treatment. FIG. 5B shows the results obtained by transfecting the 2774 cell line with an NF-kB-RE-Luc reporter plasmid, treating the transfected cell line with each of the BP5-C peptide, the BP5-mut peptide and the BP2-C peptide, and then measuring NF-kB activity in the cell line.

FIG. 6a shows the results obtained by pretreating the HUVEC cell line with 60 µg/ml of each of the peptides for 24 hours, incubating the pretreated HUVEC cell line with a fresh diluted peptide on Matrigel for 6 hours, observing the degree of tube formation of the cell line with microscope, followed by photographing.

MODE FOR INVENTION

Figure 1:
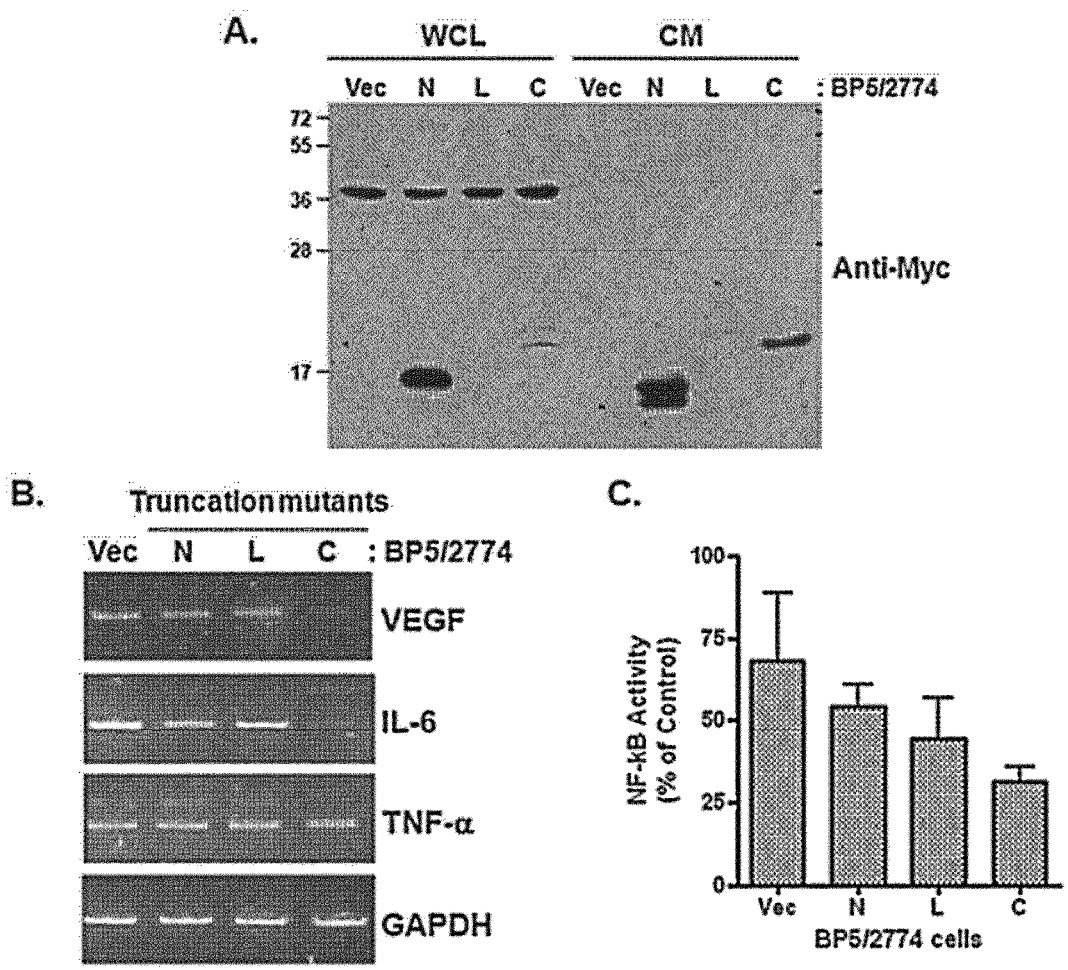
FIG. 1 shows the inhibitory effects of the C-terminal domain of IGFBP-5 against the expression of VEGF and cytokines. Specifically.

Hereinafter, the present invention will be described in further detail with reference to examples and experimental examples. It is to be understood, however, that these examples are for illustrative purposes and are not intended to limit the scope of the present invention.

Example 1

Construction of 2774 Ovarian Cancer Cell Line that Stably Expresses Each Domain of IGFBP-5

A plasmid (pSecTaq2/Hygro A, Invitrogen) (2 μg/dish (100 mm dish)) that expresses the C-terminal domain (SEQ ID NO: 1), L-domain (SEQ ID NO: 2) and N-terminal domain (SEQ ID NO: 3) of IGFBP-5 was transfected into the 2774 ovarian cancer cell line using Lipofectamine 2000 (Invitrogen). The transfection was performed according to the method provided by Invitrogen.

At 24 hours after transfection, viable colonies were collected in DMEM (+10% FBS+penicillin and hygromycin) containing hygromycin (500 μg/ml), and then positive colonies were selected by a Western blot method using Myc antibody.

Example 2

Measurement of NF-kB Activity Using Each Truncation Mutant of IGFBP-5

2274 cells that stably express the truncation mutants of IGFBP-5 were seeded into a 24-well plate, and after 24 hours, the cells were transfected with a plasmid that express each of NF-kB responding element-Luciferase (NF-kB-RE-Luc) and *Renilla* luciferase.

At 7 hours after transfection, the 2774 cells were in OPTI-MEM medium overnight in a serum-starved state. Next, the 2774 cells were lysed with lysis buffer (Promega), and then the luciferase activity of the cells was measured using a dual luciferase assay kit (Promega). The measurement of the activity performed three times in triplicate.

Example 3

Animal Experiment Using 2774 Cell Lines that Express Truncation Mutant of IGFBP-5

A 5-week-old nude mouse subcutaneously injected with $1\times10^6$ cells that express the truncation mutant of IGFBP-5, and then the tumor volume of the mice was measured at intervals of 3-4 days. In this experiment, two mice were used for each of the cell lines, and each of the cell lines was injected into two points of each mouse. This experiment was repeated three times.

Example 4

Synthesis of Peptides

The peptides used in the present invention consist of 18 amino acids and were synthesized by Peptron Co., Ltd. (Daejeon, Korea).

Specifically, a BP5-C peptide consists of amino acids 201-218 of the amino acid sequence of IGFBP-5; a BP5-mut peptide has a glycine (G)-to-alanine (A) mutation at position 203 and a glutamine (Q)-to-alanine mutation at position 209 of the amino acid sequence of IGFBP-5; a BP2-HBD peptide is a heparin-binding domain derived from IGFBP-2 and consists of amino acids 171-188 of the amino acid sequence of IGFBP-2; and a BP2-C peptide is a C-terminal domain including an IGF-1-binding domain and consists of amino acids 228-245 of the amino acid sequence of IGFBP-2. The specific sequences of the peptides are shown in Table 1 below.

TABLE 1

| Peptide | Sequence (N term→C term) | SEQ ID NO: |
|---|---|---|
| BP5-C peptide | $^{201}$RKGFYKRKQCKPSRGRKR$^{218}$ | 4 |
| BP5-mut peptide | $^{201}$RKAFYKRKACKPSRGRKR$^{218}$ | 5 |
| BP2-HBD peptide | $^{171}$KHHLGLEEPKKLRPPPAR$^{188}$ | 6 |
| BP2-C peptide | $^{228}$KHGLYNLKQCKMSLNGQR$^{245}$ | 7 |

Each of the peptides was dissolved in PBS at a concentration of 1 μg/ml, aliquoted, stored at −80° C., and kept from repeated freezing and thawing before use.

Example 5

Examination of Influence of Peptides on Expression of Cytokine by Reverse Transcription PCR (RT-PCR)

The 2274 cell line was treated overnight with various concentrations or 60 μg/ml of the peptides synthesized in Example 4, after which the cell line was additionally treated with fresh peptides for 7 hours. The cell line was treated for a total of 24 hours. Then, the cells were lysed with Trizol (Invitrogen), and RNA was isolated from the cells. cDNA was synthesized from the isolated DNA using oligo dT and super-scriptase III (Invitrogen), and then subjected to RT-PCR. Primers used in the PCR are shown in Table 2 below.

TABLE 2

| Primer | Sequence (5'→3') | SEQ ID NO: |
|---|---|---|
| VEGF F | ATGAACTTTCTGCTGTCTTGGG | 8 |
| VEGF R | CCGCCTCGGCTTGTCACATCTG | 9 |
| GAPDH F | GGAGTCCACTGGCGTCTTCACCACC | 10 |
| GAPDH R | CCTCCGACGCCTGCTTCACCACCTT | 11 |
| TNF-F | ACAAGCCTGTAGCCCATGTT | 12 |
| TNF-R | AAAGTAGACCTGCCCAGACT | 13 |
| IL-6-F | TGTAGCCGCCCCACACAGACAGCC | 14 |
| IL-6-R | GAAGAGCCCTCAGGCTGGACTGC | 15 |

In addition, the PCR was performed using EF-Taq DNA polymerase (Solgent, Daejeon, Korea) under the conditions shown in Table 3 below. However, the PCR reaction using TNF-a primers was performed for 35 cycles at an annealing temperature of 57° C.

TABLE 3

| Temp | Time | Cycle |
|---|---|---|
| 95° C. | 2 min | 1 cycle |
| 95° C. | 20 sec | 30 cycles |
| 60° C. | 40 sec | |
| 72° C. | 1 min | |

TABLE 3-continued

| Temp | Time | Cycle |
|---|---|---|
| 72° C. | 5 min | 1 cycle |
| 4° C. | ∞ | 1 cycle |

Example 6

Migration Assay

In order to examine the influence of each domain peptide of IGFBP-5 on the migration of HUVEC cells, HUVEC cells were seeded onto a 12-well plate at a density of $1\times10^5$ cells/well, and then treated with 60 μg/ml of each of the peptides for 36 hours. Specifically, the cells were treated with each of the peptides for 7 hours, and then treated overnight with a fresh peptide.

The plate was scratched with a 200-μl micropipette tip, and treated overnight with 60 μg/ml of a fresh peptide, after which the migration of the cells was observed. For this purpose, the cells were photographed under a microscope at 0 hour and the overnight time point. In addition, for a control group, cells were treated with PBS.

Example 7

Tube Formation Assay

In order to examine the influence of each domain peptide of IGFBP-5 on the tube formation of HUVEC cells, HUVEC cells were plated onto a 6-well plate at a density of $1\times10^5$ cells/well, and then treated with 60 μg/ml of each of the peptides for 24 hours.

Before a tube formation assay, growth factor-reduced Matrigel (BD Bioscience) diluted to 1:2 with PBS was added to a 24-well plate in an amount of 300 μl/well, and then solidified at 37° C. for 1 hour. The HUVEC cells treated with each of the peptides for 24 hours were trypsinized, suspended in 300 μl of EGM medium (diluted to 1:3 with EBM medium) and treated with 60 μg/ml of a fresh peptide, and then the cells were incubated on the prepared Matrigel for 6 hours. Next, the formed tubes were observed with a microscope.

Example 8

Experiment on Cancer Inhibitory Effect of IGFBP-5-Derived Peptide in Ovarian Cancer Animal Model Each of 5-week-old nude mouse was intraperitoneally injected with $5\times10^6$ 2774 cells that express GFP. At 5 days after injection of the 2774-GFP cell line, the tumor was observed with an optical image system (IVIS Spectrum, Caliper Life Sciences), after which the BP5-C peptide was intraperitoneally injected 8 times into each mouse at a dose of 30 mg/kg mouse, once at intervals of 2-3 days. At 3 days after the final injection of the peptide, the mice were observed with the optical image system and sacrificed to observe whether the tumor metastasized to other tissues, and the tumor was collected.

In this experiment, 8 mice were injected with the BP5-C peptide, and for a control group, 7 mice were injected with PBS.

Example 9

Blood Vessel Sprouting Assay Using Rat Aortic Ring

A rat aortic ring was extracted from a rat, washed twice with PBS, cut to a size of 1 mm, and then added to a 24-well plate containing matrigel. Then, each of the BP5-C, BP5mut, BP2-HBD and BP2-C peptide was diluted in EGM medium (Lonza) at a concentration of 60 μg/ml, and the rat aortic ring was treated with each of the peptide-containing media and incubated at 37° C. for 6 days. During the treatment period, the rat aortic ring was treated with a fresh peptide (diluted in EGM medium at 60 μg/ml) once at intervals of 2 days. Then, the blood vessels were observed with a microscope.

Experimental Example 1

Inhibitory Effect of C-Terminal Domain of IGFBP-5 Against Expression of VEGF and Cytokines IGFBP-5 consists largely of three domains (N-terminal domain, C-terminal domain and L-domain). The present inventors performed the following experiment in order to examine whether each of the domains of IGFBP-5 can cancer or angiogenesis by inhibiting the VEGF and cytokines such as IL-6 and TNF-alpha.

Specifically, the expression level of each truncation domain in an ovarian cancer cell line that stably expresses each domain of IGFBP-5 was analyzed by Western blotting using WCL (whole cell lysate) and CM (conditioned media) (FIG. 1A). As can be seen in FIG. 1A, each of the domains of IGFBP-5 was well expressed in the 2774 cell line and well secreted into the media.

Total RNA was isolated from the 2774 cells, and then RT-PCR for VEGF, IL-6 and TNF-alpha (TNF-a) was performed. As a result, it was shown that the expression of VEGF, IL-6, TNF-a genes in the 2274 cell line expressing the C-terminal domain was significantly inhibited (FIG. 1B). In addition, the influence of the domains on NF-kB activity (that is a signaling pathway important for cancer development and a downstream signal of IL-6) was examined, and as a result, the activity of NF-kB in the 2774 cell line expressing the C-terminal domain was also significantly inhibited (FIG. 1C).

In conclusion, the expression of the C-terminal domain of IGFBP-5 inhibits the gene expression of VEGF and cytokines such as IL-6 and TNF-α and inhibits NF-kB activity that is a signaling pathway important for cancer growth.

Thus, the above results suggest that the C-terminal domain of IGFBP-5 can inhibit cancer growth or angiogenesis by specifically inhibiting the expression of VEGF, IL-6 and TNF-α and inhibiting NF-kB activity.

Experimental Example 2

Cancer Growth Inhibition of C-Terminal Domain of IGFBP-5

Figure 2A:
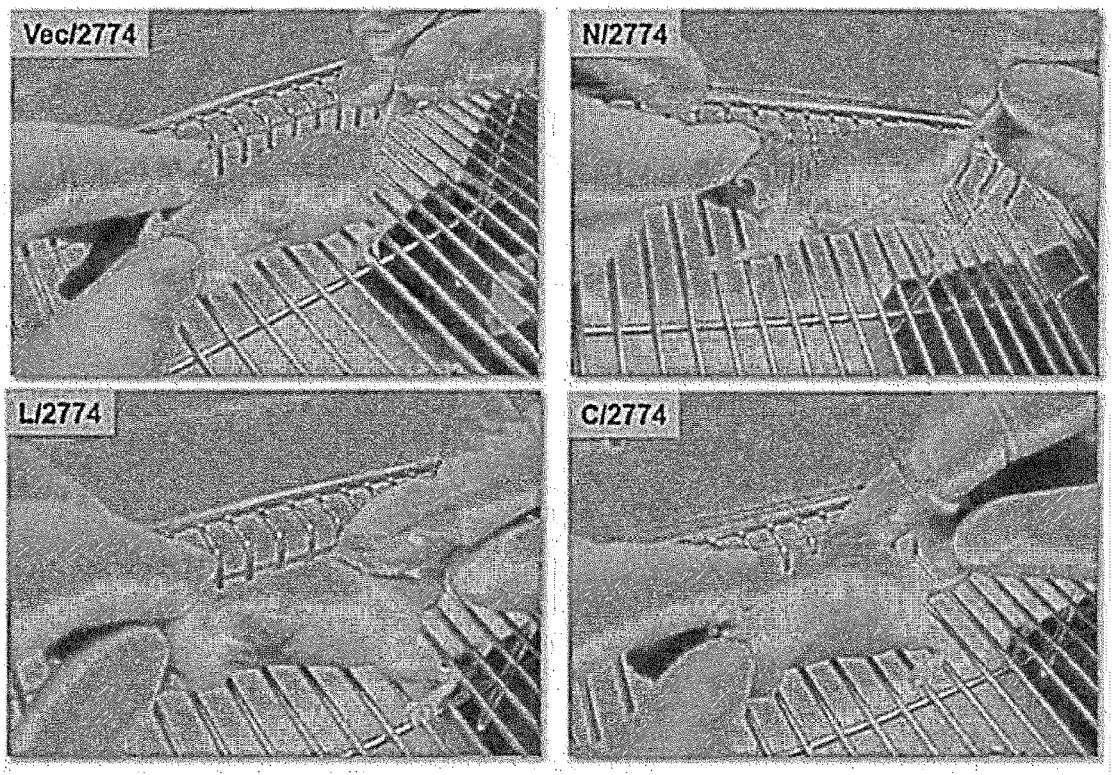
FIGS. 2a and b show the inhibitory effect of the C-terminal domain of IGFBP-5 against tumor growth. Specifically.

In order to examine the influence of each domain of IGFBP-5, particularly the C-terminal domain that inhibits the expression of VEGF and cytokines such as IL-6, on cancer growth, the ovarian cancer cell line 2774 that expresses each domain of IGFBP-5 was subcutaneously injected into nude mice, and then cancer growth in the mice was observed. The results of the observation are shown in FIGS. 2a and b. Specifically, FIG. 2a is a photograph showing the results of observing cancer growth after injecting the nude mice subcutaneously with the 2774 ovarian cancer cell line that expresses each domain of IGFBP-5, and FIG. 2b is a graph showing the growth of the tumor observed as shown in FIG. 2a and shows a photograph of the tumor collected from each mouse.

Figure 2B:
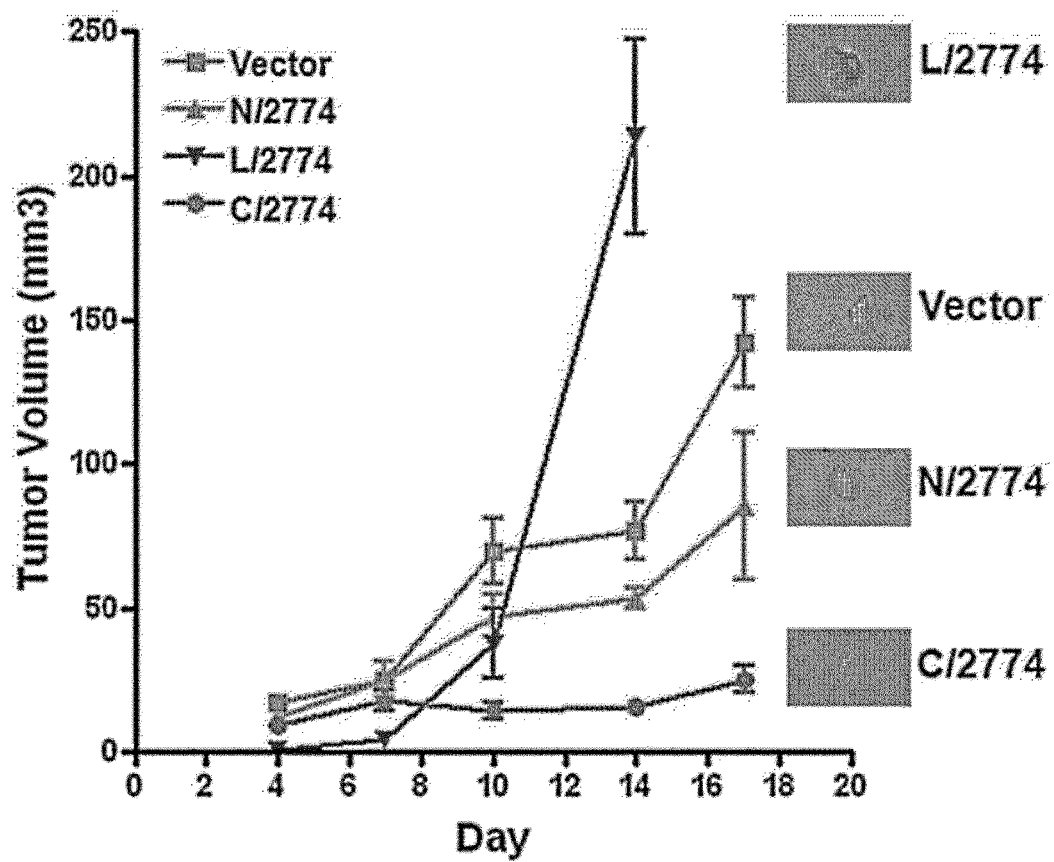
FIG. 2b is a graph showing the growth of the tumor and shows a photograph of the tumor collected from each mouse. The right side of each graph shows a photograph of the tumor collected from the animal, and in FIG. 2b, N/2774, L/2774 and C/2774 indicate the 2774 cell lines that stably express the N-terminal domain, L-domain and C-terminal domain of IGFBP-5, respectively.

As a result, it was shown that the growth of cancer in the mouse injected with the 2774 cells that the C-terminal domain was significantly inhibited compared to that in the mouse injected with Vec/2774, and particularly, the growth of cancer in the mouse (C/2774) treated with the C-terminal domain was more effectively inhibited compared to that in the mice treated with the L-domain and the N-terminal domain (FIGS. 2a and 2b).

Thus, the above results together with the results of Experimental Example 1 suggest that the C-terminal domain of IGFBP-5 can inhibit angiogenesis important for cancer growth by inhibiting the expression of the VEGF gene and inhibit cancer growth by inhibiting NF-kB-related signals important for cancer growth.

Experimental Example 3

Examination of Function of Peptide Derived from C-Terminal Domain of IGFBP-5

A peptide (BP5-C) corresponding to the 201-218 amino acid domain of the C-terminal domain of IGFBP-5 was synthesized. The influence of the BP5-C peptide on the expression of VEGF, IL-6 and TNF-α genes was analyzed by RT-PCR, and the results of the analysis are shown in FIG. 3.

As a result, it was shown that the BP5-C peptide inhibited the expression of VEGF, IL-6 and TNF-α genes in a concentration-dependent manner (FIG. 3A). In addition, the BP5-C peptide effectively inhibited NF-kB activity (FIG. 3B).

The above results are consistent with the results obtained in the C/2774 stable cells that express the C-terminal domain of IGFBP-5. These results suggest that the 201-218 amino acid domain of the C-terminal domain of IGFBP-5 plays an important role in inhibiting the expression of VEGF and IL-6 gene in the C/2774 cell line by the C-terminal domain of IGFBP-5.

Experimental Example 4

Inhibition of VEGF Gene by HBD (Heparin-Binding Domain) of IGFBP-5

The 201-218 amino acid domain of the C-terminal domain of IGFBP-5 comprises an IGF-1-binding domain and a heparin-binding domain (HBD). Particularly, the IGF-1-binding domain is known to bind to IGF-I so as to interfere with the binding of IGF-I to IGF-I receptor, thereby inhibiting VEGF expression and cancer growth. Thus, in order to examine whether the effect of the BP5-C peptide in the above Experimental Examples is attributable to the IGF-1-binding domain, a peptide (BP5-mut; 203A, 209A) was synthesized in which two amino acids (glycine (G) at position 203 and glutamine (Q) at position 209, which play an important role in IGF-I binding) in the IGF-1-binding domain were mutated to alanine (A). In addition, peptides corresponding to the C-terminal domain (BP2-C; containing an IGF-1-binding domain) of IGFBP-2, known to stimulate cancer growth among the IGFBP family, and the heparin-binding domain (BP2-HBD) of IGFBP-2, were synthesized in order to examine whether the above-described effect is the specific effect of the IGFBP-5 HBD or IGF-1-binding domain. The results are shown in FIG. 5.

The 2774 ovarian cancer cell line was treated with each of the peptides, and the expression patterns of VEGF, IL-6 and TNF-α genes in the cell line were analyzed by RT-PCR. As a result, the BP5-C and BP5-mut peptides inhibited the expression of VEGF and IL-6 genes (FIG. 5A), whereas groups treated with PBS or the peptides derived from IGFBP-2 showed no change in the expression patterns. In addition, the BP5-C and BP5-mut peptides inhibited NF-kB activity (FIG. 5B).

Thus, the above results suggest that the heparin-binding domain derived from IGFBP-5 plays an important role in inhibiting the expression of VEGF and IL-6 genes and inhibiting NF-kB activity.

Experimental Example 5

Inhibitory Effect of Heparin-Binding Domain of IGFBP-5 Against Tube Formation and Migration Of HUVEC Cell Line Cancer cells produce new blood vessels in order to use nutrients important for cancer cell growth. It is known that VEGF particularly plays an important role in this angiogenesis. Thus, it appears that, because the heparin-binding domain of IGFBP-5 inhibits the major regulator VEGF gene of angiogenesis, the IGFBP-5 peptide of the present invention can inhibit angiogenesis. Thus, the influence of the IGFBP-5 peptide on the tube formation of HUVEC (human umbilical vein endothelial cell) was examined.

Figure 6A:
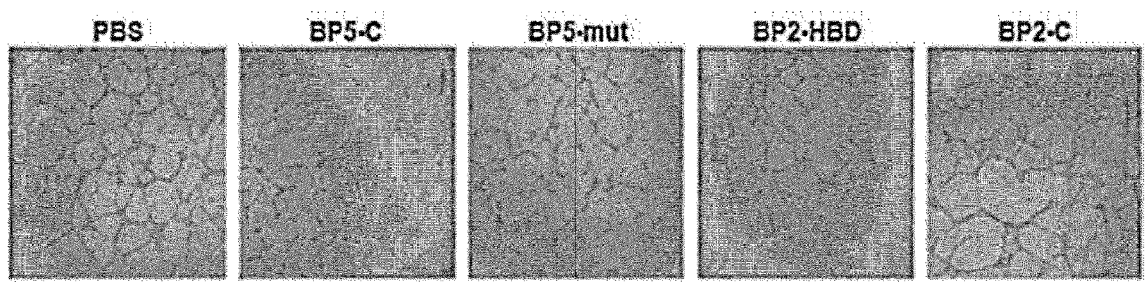
FIGS. 6a and b show the inhibitory effect of the heparin-binding domain of IGFBP-5 against the tube formation and migration of HUVEC. Specifically.

As a result, it was shown that the treatment of HUVEC with the BP5-C peptide and the BP5-mut peptide inhibited tube formation, whereas PBS, the BP2-HBD peptide or the BP2-C peptide showed no influence on tube formation (FIG. 6a).

In addition, because cancer cells migrate for metastasis to other tissues, the migration of HUVEC was analyzed in order to examine the influence of the inventive peptide on the migration of cancer cells.

Figure 6B:
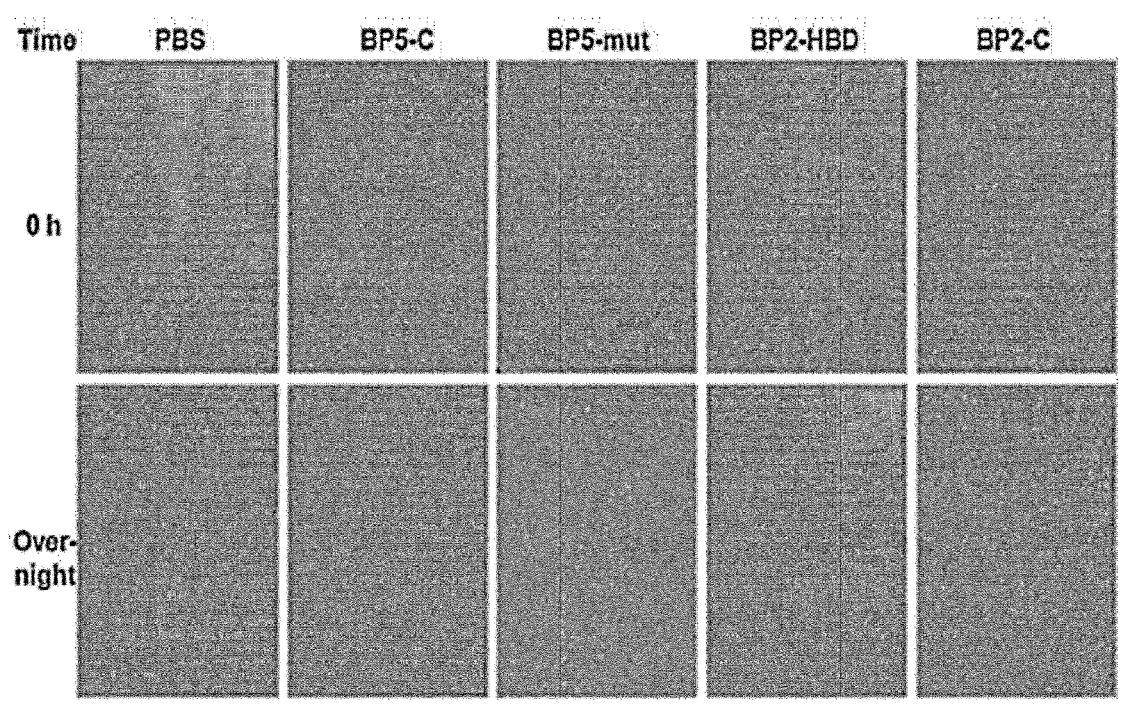
FIG. 6b shows the effect of each of the peptides against the migration of HUVEC. In an experiment regarding FIG. 6b, HUVEC cells were added to a 12-well plate at a density of $1\times10^5$ cells/well and treated with 60 µg/ml of each peptide for 36 hours, after which each well was scratched with a 200 µg/ml pipette tip, and then photographed, and the photographs were indicated as "0h". Next, the cells were treated with 60 µg/ml of a fresh diluted peptide and incubated overnight, after which the degree of migration of the HUVEC cell line was observed with a microscope.

As a result, it was shown that the BP5-C peptide or the BP5-mut peptide inhibited the migration of HUVEC, whereas PBS, the BP2-HBD peptide or the BP2-C peptide did not inhibit the migration of HUVEC (FIG. 6b).

The above results suggest that the heparin-binding domain derived from IGFBP-5 plays an important role in the inhibition of angiogenesis and cancer metastasis.

Experimental Example 6

Cancer Inhibitory Effect of Peptide Derived from C-Terminal Domain of IGFBP-5

Figure 7:
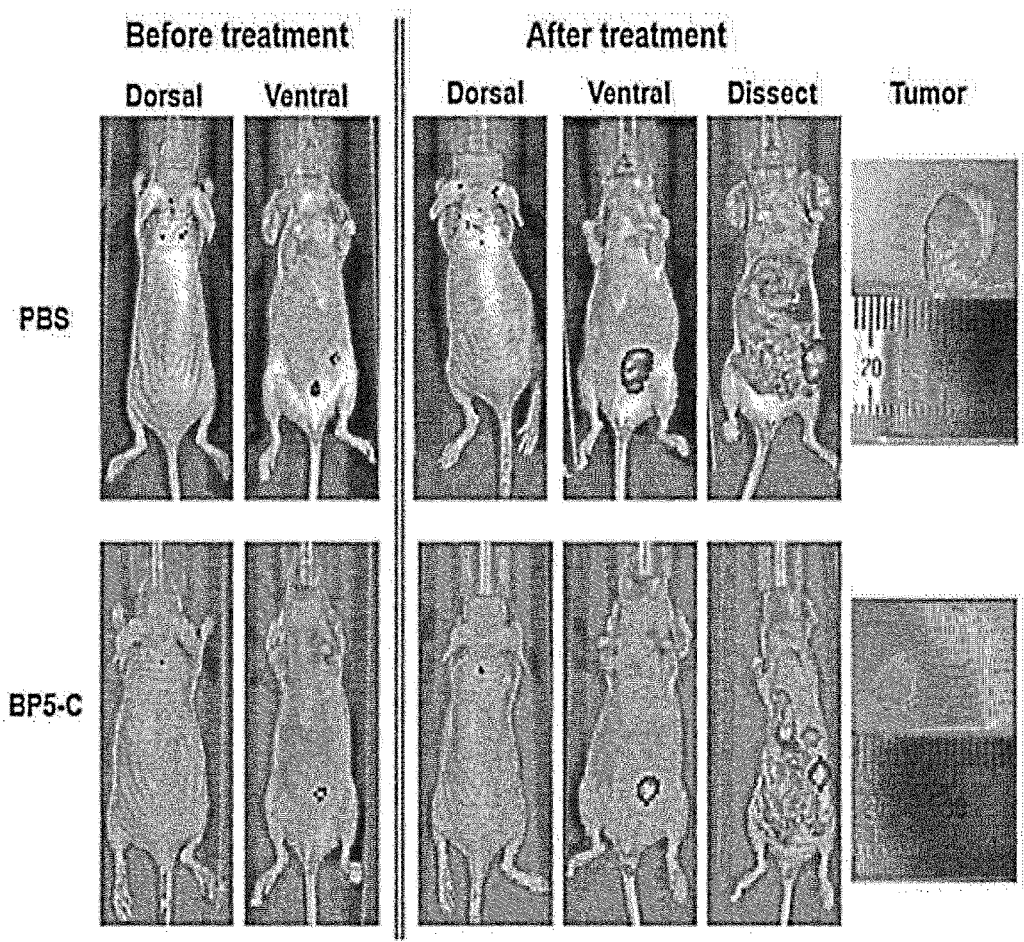
FIG. 7 shows the inhibitory effect of the C-terminal domain of IGFBP-5 against cancer growth. To examine the influence of the C-terminal domain peptide (BP5-C) of IGFBP-5 on tumor growth, a 2774-GFP cell line was injected intraperitoneally into a nude mouse to make an ovarian cancer animal model. The peptide (30 mg/kg) was injected intraperitoneally 8 times into the animal model at intervals of 2-3 days, followed by observation of the tumor. The dorsal and ventral portion of the mouse was optically imaged before and after injection with the peptide or PBS. After the final injection of the peptide, the mouse was sacrificed, the abdominal cavity was dissected, and the tumor was collected and compared with the tumor of a mouse injected with PBS.

The BP5-C peptide derived from the C-terminal domain of IGFBP-5 was intraperitoneally injected 8 times into ovarian cancer animal models at intervals of 2-3 days, and then the tumors were observed. The results of the observation are shown in FIG. 7.

As a result, tumor growth in the animals injected with the BP5-C peptide was significantly inhibited compared to that in the control group. The tumors were collected and the volumes thereof were compared, and as a result, the tumor volume of the animals injected with the BP5-C peptide was significantly reduced compared to the animals injected with PBS. In view of the above Experimental Examples, it is believed that the tumor inhibitory effect of the BP5-C peptide of the present invention is attributable to the inhibition of angiogenesis by the heparin-binding domain.

Experimental Example 7

Examination of the Inventive Peptide Against Blood Vessel Sprouting Using Rat Aortic Ring Using the method of Example 9, the influence of the inventive peptides (BP5-C and BP5-mut) and the comparative peptides (BP2-HBD and BP2-C) on blood vessel sprouting was examined.

Figure 8:
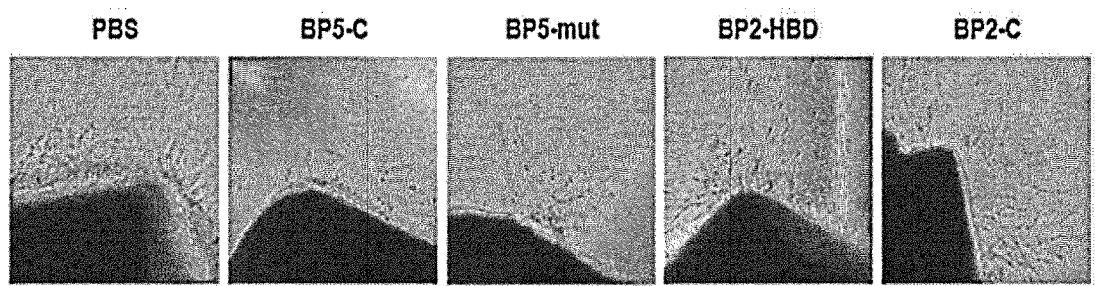
FIG. 8 shows the results obtained by examining the effects of the BP5 peptides against blood vessel sprouting using rat aortic rings.

As a result, as shown in FIG. 8, the two peptides of the present invention all effectively inhibited blood vessel sprouting, unlike the comparative peptides.

Thus, the above results indicate that the inventive peptide comprising the heparin-binding domain of IGFBP-5 can be effectively used as an angiogenesis inhibitor and an agent for preventing or treating angiogenesis-related diseases such as cancer.

Although the preferred embodiments of the present invention have been described for illustrative purposes, those skilled in the art will appreciate that various modifications, additions and substitutions are possible, without departing from the scope and spirit of the invention as disclosed in the accompanying claims.

---

What is claimed is:

1. A method for inhibiting angiogenesis, comprising administering an isolated peptide consisting of the heparin-binding domain of insulin-like growth factor-binding protein-5 (IGFBP-5) to a subject in need thereof.

2. The method of claim 1, wherein the peptide consists of an amino acid sequence selected from the group consisting of SEQ ID NO: 4 and SEQ ID NO: 5.

3. The method of claim 1, wherein the peptide has an effect of reducing the expression or signaling of VEGF (vascular endothelial growth factor).

4. The method of claim 1, wherein the subject in need thereof has a disease selected from the group consisting of diabetic retinopathy, retinopathy of prematurity, neovascular glaucoma and proliferative retinopathy.

5. A method for treating ovarian cancer by inhibition of angiogenesis, comprising administering an isolated peptide consisting of the heparin-binding domain of insulin-like growth factor-binding protein-5 (IGFBP-5) to a subject in need thereof.

6. The method of claim 5, wherein the peptide consists of an amino acid sequence selected from the group consisting of SEQ ID NO: 4 and SEQ ID NO: 5.

* * * * *

SEQUENCE LISTING

```
<160> NUMBER OF SEQ ID NOS: 18

<210> SEQ ID NO 1
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IGFBP5-C terminal domain

<400> SEQUENCE: 1

Gln Gly Pro Cys Arg Arg His Met Glu Ala Ser Leu Gln Glu Leu Lys
1               5                   10                  15

Ala Ser Pro Arg Met Val Pro Arg Ala Val Tyr Leu Pro Asn Cys Asp
            20                  25                  30

Arg Lys Gly Phe Tyr Lys Arg Lys Gln Cys Lys Pro Ser Arg Gly Arg
        35                  40                  45

Lys Arg Gly Ile Cys Trp Cys Val Asp Lys Tyr Gly Met Lys Leu Pro
    50                  55                  60

Gly Met Glu Tyr Val Asp Gly Asp Phe Gln Cys His Thr Phe Asp Ser
65                  70                  75                  80

Ser Asn Val Glu

<210> SEQ ID NO 2
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IGFBP-5 L domain

<400> SEQUENCE: 2

Leu Asn Glu Lys Ser Tyr Arg Glu Gln Val Lys Ile Glu Arg Asp Ser
1               5                   10                  15

Arg Glu His Glu Glu Pro Thr Thr Ser Glu Met Ala Glu Glu Thr Tyr
            20                  25                  30

Ser Pro Lys Ile Phe Arg Pro Lys His Thr Arg Ile Ser Glu Leu Lys
        35                  40                  45

Ala Glu Ala Val Lys Lys Asp Arg Arg Lys Lys Leu Thr Gln Ser Lys
    50                  55                  60

Phe Val Gly Gly Ala Glu Asn Thr Ala His Pro Arg Ile Ile Ser Ala
65                  70                  75                  80

Pro Glu Met Arg Gln Glu Ser Glu
            85
```

<210> SEQ ID NO 3
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IGFBP-5 N-terminal domain

<400> SEQUENCE: 3

Leu Gly Ser Phe Val His Cys Glu Pro Cys Asp Glu Lys Ala Leu Ser
1               5                   10                  15

Met Cys Pro Pro Ser Pro Leu Gly Cys Glu Leu Val Lys Glu Pro Gly
            20                  25                  30

Cys Gly Cys Cys Met Thr Cys Ala Leu Ala Glu Gly Gln Ser Cys Gly
        35                  40                  45

Val Tyr Thr Glu Arg Cys Ala Gln Gly Leu Arg Cys Leu Pro Arg Gln
    50                  55                  60

Asp Glu Glu Lys Pro Leu His Ala Leu Leu His Gly Arg Gly Val Cys
65                  70                  75                  80

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: BP5-C peptide

<400> SEQUENCE: 4

Arg Lys Gly Phe Tyr Lys Arg Lys Gln Cys Lys Pro Ser Arg Gly Arg
1               5                   10                  15

Lys Arg

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: BP5-mut peptide

<400> SEQUENCE: 5

Arg Lys Ala Phe Tyr Lys Arg Lys Ala Cys Lys Pro Ser Arg Gly Arg
1               5                   10                  15

Lys Arg

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: BP2-HBD peptide

<400> SEQUENCE: 6

Lys His His Leu Gly Leu Glu Glu Pro Lys Lys Leu Arg Pro Pro Pro
1               5                   10                  15

Ala Arg

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: BP2-C peptide

<400> SEQUENCE: 7

Lys His Gly Leu Tyr Asn Leu Lys Gln Cys Lys Met Ser Leu Asn Gly
1               5                   10                  15

Gln Arg

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      VEGF F primer

<400> SEQUENCE: 8
atgaactttc tgctgtcttg gg                                          22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      VEGF R primer

<400> SEQUENCE: 9
ccgcctcggc ttgtcacatc tg                                          22

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      GAPDH F primer

<400> SEQUENCE: 10
ggagtccact ggcgtcttca ccacc                                       25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      GAPDH R primer

<400> SEQUENCE: 11
cctccgacgc ctgcttcacc acctt                                       25

<210> SEQ ID NO 12
<211> LENGTH: 20
<212> TYPE: DNA
<213> ORGANISM: Artificial Sequence
<220> FEATURE:

-continued

<223> OTHER INFORMATION: Description of Artificial Sequence: Synthetic
      TNF-F primer

<400> SEQUENCE: 12
acaagcctgt agcccatgtt                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      TNF-R primer

<400> SEQUENCE: 13
aaagtagacc tgcccagact                                                   20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      IL-6-F primer

<400> SEQUENCE: 14
tgtagccgcc ccacacagac agcc                                              24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      IL-6-R primer

<400> SEQUENCE: 15
gaagagccct caggctggac tgc                                               23

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 16

Arg Lys Xaa Phe Tyr Lys Arg Lys Xaa Cys Lys Pro Ser Arg Gly Arg
1               5                   10                  15

Lys Arg

<210> SEQ ID NO 17
<211> LENGTH: 328
<212> TYPE: PRT
<213> ORGANISM: Homo sapiens

<400> SEQUENCE: 17

Met Leu Pro Arg Val Gly Cys Pro Ala Leu Pro Leu Pro Pro Pro Pro

```
               1               5                  10                 15
            Leu Leu Pro Leu Leu Pro Leu Leu Leu Leu Leu Gly Ala Ser Gly
                           20                 25                 30

Gly Gly Gly Gly Ala Arg Ala Glu Val Leu Phe Arg Cys Pro Cys
                           35                 40                 45

Thr Pro Glu Arg Leu Ala Ala Cys Gly Pro Pro Val Ala Pro Pro
                50                      55                 60

Ala Ala Val Ala Val Ala Gly Gly Ala Arg Met Pro Cys Ala Glu
            65                      70                 75                 80

Leu Val Arg Glu Pro Gly Cys Gly Cys Ser Val Cys Ala Arg Leu
                                85                 90                 95

Glu Gly Glu Ala Cys Gly Val Tyr Thr Pro Arg Cys Gly Gln Gly Leu
                           100                105                110

Arg Cys Tyr Pro His Pro Gly Ser Glu Leu Pro Leu Gln Ala Leu Val
                           115                120                125

Met Gly Glu Gly Thr Cys Glu Lys Arg Arg Asp Ala Glu Tyr Gly Ala
                           130                135                140

Ser Pro Glu Gln Val Ala Asp Asn Gly Asp Asp His Ser Glu Gly Gly
            145                     150                155                160

Leu Val Glu Asn His Val Asp Ser Thr Met Asn Met Leu Gly Gly Gly
                                165                170                175

Gly Ser Ala Gly Arg Lys Pro Leu Lys Ser Gly Met Lys Glu Leu Ala
                           180                185                190

Val Phe Arg Glu Lys Val Thr Glu Gln His Arg Gln Met Gly Lys Gly
                           195                200                205

Gly Lys His His Leu Gly Leu Glu Glu Pro Lys Lys Leu Arg Pro Pro
                           210                215                220

Pro Ala Arg Thr Pro Cys Gln Gln Glu Leu Asp Gln Val Leu Glu Arg
            225                     230                235                240

Ile Ser Thr Met Arg Leu Pro Asp Glu Arg Gly Pro Leu Glu His Leu
                                245                250                255

Tyr Ser Leu His Ile Pro Asn Cys Asp Lys His Gly Leu Tyr Asn Leu
                           260                265                270

Lys Gln Cys Lys Met Ser Leu Asn Gly Gln Arg Gly Glu Cys Trp Cys
                           275                280                285

Val Asn Pro Asn Thr Gly Lys Leu Ile Gln Gly Ala Pro Thr Ile Arg
                           290                295                300

Gly Asp Pro Glu Cys His Leu Phe Tyr Asn Glu Gln Glu Ala Arg
            305                     310                315                320

Gly Val His Thr Gln Arg Met Gln
                                325

<210> SEQ ID NO 18
<211> LENGTH: 272
<212> TYPE: PRT
<213> ORGANISM: Homo sapiens

<400> SEQUENCE: 18

Met Val Leu Leu Thr Ala Val Leu Leu Leu Ala Ala Tyr Ala Gly
1               5                  10                 15

Pro Ala Gln Ser Leu Gly Ser Phe Val His Cys Glu Pro Cys Asp Glu
                20                 25                 30

Lys Ala Leu Ser Met Cys Pro Pro Ser Pro Leu Gly Cys Glu Leu Val
                35                 40                 45
```

-continued

```
Lys Glu Pro Gly Cys Gly Cys Cys Met Thr Cys Ala Leu Ala Glu Gly
    50              55                  60
Gln Ser Cys Gly Val Tyr Thr Glu Arg Cys Ala Gln Gly Leu Arg Cys
65              70                  75                  80
Leu Pro Arg Gln Asp Glu Glu Lys Pro Leu His Ala Leu Leu His Gly
            85                  90                  95
Arg Gly Val Cys Leu Asn Glu Lys Ser Tyr Arg Glu Gln Val Lys Ile
            100                 105                 110
Glu Arg Asp Ser Arg Glu His Glu Glu Pro Thr Thr Ser Glu Met Ala
            115                 120                 125
Glu Glu Thr Tyr Ser Pro Lys Ile Phe Arg Pro Lys His Thr Arg Ile
    130                 135                 140
Ser Glu Leu Lys Ala Glu Ala Val Lys Lys Asp Arg Arg Lys Lys Leu
145                 150                 155                 160
Thr Gln Ser Lys Phe Val Gly Gly Ala Glu Asn Thr Ala His Pro Arg
                165                 170                 175
Ile Ile Ser Ala Pro Glu Met Arg Gln Glu Ser Glu Gln Gly Pro Cys
            180                 185                 190
Arg Arg His Met Glu Ala Ser Leu Gln Glu Leu Lys Ala Ser Pro Arg
            195                 200                 205
Met Val Pro Arg Ala Val Tyr Leu Pro Asn Cys Asp Arg Lys Gly Phe
    210                 215                 220
Tyr Lys Arg Lys Gln Cys Lys Pro Ser Arg Gly Arg Lys Arg Gly Ile
225                 230                 235                 240
Cys Trp Cys Val Asp Lys Tyr Gly Met Lys Leu Pro Gly Met Glu Tyr
                245                 250                 255
Val Asp Gly Asp Phe Gln Cys His Thr Phe Asp Ser Ser Asn Val Glu
            260                 265                 270
```